United States Patent [19]

Springer

[11] 4,427,653

[45] Jan. 24, 1984

[54] METHOD OF MAKING MONOCLONAL ANTIBODIES

[75] Inventor: Timothy A. Springer, Brookline, Mass.

[73] Assignee: President and Fellows of Harvard College, Cambridge, Mass.

[21] Appl. No.: 228,063

[22] Filed: Jan. 26, 1981

[51] Int. Cl.³ .................. C12P 21/00; A61K 39/00; C12N 5/00

[52] U.S. Cl. .................................... 424/85; 424/88; 435/68; 435/172; 435/240; 435/948

[58] Field of Search ............... 435/68, 172, 240, 241; 424/85; 435/7, 34

[56] References Cited

PUBLICATIONS

Pearson et al., "Dissection of Complex Antigenic Mixtures Using Monoclonal Antibodies and Two-Dimensional Gel Electrophoresis", *Analytical Biochemistry*, vol. 101, (Jan. 15, 1980), pp. 377–386.

Hurn et al., "Production of Reagent Antibodies", *Methods in Enzymology*, vol. 70 (1980), pp. 135–142.

Mellman et al., "Purification of a Functional Mouse Fc Receptor Through the Use of a Monoclonal Antibody", *Journal of Experimental Medicine*, (Oct. 1980), pp. 1048–1049.

Milstein, "Monoclonal Antibodies", *Scientific American*, (Oct. 1980), pp. 73–74.

Springer, "Monoclonal Antibody Analysis of Complex Biological Systems", Journal of Biological Chemistry 256(8), (1981), pp. 3833–3839.

Anderson et al., "Isolation of Tumor-Associated Macromolecules Using Immunosubtraction", Federation Proceedings 32(3), (1973), Abst. #4165.

Middleton et al., Fed. Proc. (Abstr.), vol. 39, 3464 (1980).

Kennett et al., Top. Micro. Immunol., vol. 81, 77 et seq. (1978).

*Primary Examiner*—Alvin E. Tanenholtz
*Assistant Examiner*—John Edward Tarcza

[57] ABSTRACT

Methods featuring, in one aspect, a method of preparing an antigen or mixture of antigens substantially free of antigens specific to at least two monoclonal antibodies, said method involving contacting an antigen mixture with one or more previously-isolated monoclonal antibodies to form complexes between those antibodies and antigens present in the mixture specific to the antibodies, removing the complexes from the antigen mixture to yield a partially purified antigen mixture, immunizing an animal with the partially purified antigen mixture, fusing spleen cells from the immunized animal to myeloma cells to form hybridomas capable of producing additional monoclonal antibodies, culturing said hybridomas to produce said additional monoclonal antibodies, contacting a sample of the partially purified antigen mixture with said additional monoclonal antibodies to form complexes between said additional monoclonal antibodies and antigens present in the antigen mixture specific to the additional monoclonal antibodies, and removing the complexes from the antigen mixture.

1 Claim, No Drawings

METHOD OF MAKING MONOCLONAL ANTIBODIES

The invention described herein was made in part in the course of work under a grant from the National Institute of Health.

This invention relates to antibodies and, more specifically, to specific monoclonal antibodies (MAb) produced by fused cell hybrids (hybridomas).

In recent years fused cell hybrids of spleen cells and myeloma cells have been used to produce antibodies specific to the surface antigens of various cells. For example, Koprowski et al. U.S. Pat. No. 4,172,124 describes a method involving immunizing an animal with tumor cells and then fusing the immunized animal's spleen cells with myeloma cells to form hybridomas capable of producing antibodies specific to the tumor.

More recently, rather than whole cells, cell fractions, e.g., cell membranes, have been used as antigen sources for immunizing animals. When such a cell fraction is used, it is often desirable to identify and isolate only one or a few specific antigens of the large number of antigens present in the fraction, and to obtain monoclonal antibodies specific to those few antigens. This is the case, for example, when the majority of the antigens in the fraction are of little interest, either because they are common to several types of cells, or because they have been previously isolated and identified. The isolation of specific antigens, and of antibodies specific to those antigens, has until now been difficult, however, involving the laborious and often complex screening of hundreds or even thousands of hybrid cultures. This difficulty is compounded by the fact that the undesired antigens in a given antigen mixture frequently tend to be immunodominant, i.e., they can non-specifically suppress the immune response of an animal to other antigens in the mixture by means of antigenic competition.

Several attempts have been made to narrow the range of MAb elicited in cell hybridization procedures. For example, Middleton et al. (1980) *Fed. Proc.* (abstr.) 39, 3464 discloses a method of inducing tolerance to B lymphocytes in order to enhance the percentage of T cell-specific hybridomas. Kennett et al. (1978) *Top. Micro. Immunol.* 81, 77 describes a method for increasing specificity involving blocking surface antigens of one type of cell with whole antiserum to another type of cell. These methods are not entirely satisfactory, however, in part because they cannot be used to continually narrow the response to unidentified cell surface antigens in further hybridization experiments.

This invention provides a method of eliminating undesired antigens specific to at least two monoclonal antibodies. The method involves contacting an antigen mixture with one or more previously-isolated monoclonal antibodies to form complexes between those antibodies and antigens present in the mixture specific to the antibodies, removing the complexes from the antigen mixture to yield a partially purified antigen mixture, immunizing an animal with the partially purified antigen mixture, fusing spleen cells from the immunized animal to myeloma cells to form hybridomas, culturing the hybridomas to produce the additional monoclonal antibodies, contacting a sample of the partially purified antigen mixture with said additional monoclonal antibodies to form complexes between said additional monoclonal antibodies and antigens present in the antigen mixture specific to the additional monoclonal antibodies, and removing the complexes from the antigen mixture. The process can be repeated indefinitely, each time yielding an antigen mixture free of antigens specific for previously produced monoclonal antibodies.

The antigen monoclonal antibody complexes can be removed from the antigen mixture using any suitable method. A preferred method is to immobilize the monoclonal antibody on a column prior to contacting the antibody with the antigen mixture. Another method is to remove complexes by a sizing technique, such as gel permeation chromatography. Still another method involves linking the monoclonal antibody non-covalently to a support which is bound to a column. Such a support can be another antibody, or *Staphlococcus aureus* protein A, which is specific for the Fc portion of most antibodies. Yet another method is to remove complexes using electrophoresis.

The following specific example is intended to more fully illustrate the present invention, without acting as a limitation upon its scope.

EXAMPLE

The procedure described below was followed in order to isolate antigens specific to the macrophage cell surface, while eliminating those antigens common to several non-macrophage cell types. The scheme involved macrophage membrane preparation, detergent solubilization, lectin affinity purification to obtain a glycoprotein fraction, immunoadsorbent removal of previously identified antigens on immunoadsorbent columns, immunization, cell fusion, and monoclonal antibody collection.

Purification of Macrophage Membranes

Peritoneal exudate cells from 25 C57BL/6 mice (Jackson Laboratory, Bar Harbor, ME) were collected 3 days after injection of 1.5 ml Brewer's thioglycollate medium (Difco). Cells ($8 \times 10^8$ total, 84% macrophages, 2.5% neutrophils, 7.5% eosinophils, 4.5% lymphocytes, and 1.5% RBC by Wright's stain) were washed and suspended in 20 ml PBS containing 0.5 mM phenylmethyl sulfonyl fluoride (PMSF, diluted from a 50 mM solution in ethanol) and broken by $N_2$ cavitation after pressurization at 600 psi for 10 min. After centrifugation at 1,500 g$\times$5 min., the pellet was homogenized using a teflon pestle in 30 ml of the same buffer and centrifuged at 1,500 g$\times$5 min. The two 1,500 g supernatants were combined, and the 48,000 g$\times$30 min pellet (crude membranes, 34.8 $A_{280}$-$A_{310}$ units) was suspended in 2 ml PBS+PMSF.

Membrane Solubilization and Lectin Affinity Purification

All solubilization and purification steps were carried out at 4° C.

The membrane suspension from the previous purification step was solubilized with two volumes of 1.25% NaDC in 0.01 M tris HCl at pH 8.2 and the solution was centrifuged at 100,000 g for 45 min. The supernatant was applied to 2.4 ml of 4.6 mg *L. culinaris* lectin/ml of Sepharose CL-4B (Pharmacia) packed in a 3 ml syringe according to the method described in Hayman et al. (1972) *Biochem. Biophys. Res. Comm.* 47, 923. The syringe was then washed with 21 ml 0.1% NaDC 0.01 M tris HCl at pH 8.2. Glycoproteins were eluted with 9 ml 5% α-methyl-D-mannoside in the same buffer at 3 ml/h and then with 6 ml at 1 ml/h. The 3 peak fractions were pooled, dialyzed against 0.1% NaDC, 0.01 M tris HCl at pH 8.2, concentrated on Sephadex G-200 (Pharmacia), and sufficient 5% NaDC was added to bring the NaDC concentration up to 0.5%.

Immunoadsorbent Purification

Prior to using the partially purified antigen mixture described above to immunize animals, the undesired heat stable antigens (HSA) and common leucocyte antigen (CLA) were removed using MAb immunoadsorbents.

The MAb immunoadsorbents were derived from the hybridoma cell lines M1/69.16, M1/89.18, M1/70, and M1/9.3, all of which have been deposited with the Cell Line Distribution Center, Salk Institute, P. O. Box 1809, San Diego, Calif. Cells from these cell lines were subcloned at least once, and then the cells were grown to maximum density in 5% fetal calf serum in Dulbecco's modified Eagle's Medium. The MAb to be used as immunoadsorbent was obtained from the spent medium.

Purification of MAb and Coupling of MAb to Sepharose

All MAb purification steps were carried out at 4° C. After each step, rat IgG was determined by Mancini radial immunodiffusion using rabbit anti-rat Fab, as described in Ouchterlony et al. (1978) in *Handbook of Experimental Immunology*, Weir, ed., Oxford, p. 19.10.

To 0.5-1 L of the spent culture medium described above was added sufficient solid $(NH_4)_2SO_4$ to bring its concentration in the medium up to 2.2 M. The medium was centrifuged at 10,000 g, and the pellet was dialyzed against 0.1 M tris HCl (pH 7 at 20° C.) and applied to a DEAE cellulose column (DE-52, Reeve and Angell) at 8 mg protein per ml DE-52. The protein was immediately eluted with 6 column volumes of 0.1 M tris-HCl, pH 7.8, containing a linear gradient of 0-0.05 M NaCl. Most MAb eluted in the flowthrough volume.

Peak fractions were pooled, concentrated by ultrafiltration and applied to a 4×120 cm Sephadex G-200 column. Concentrated MAb samples, which were typically 90-100% pure as shown by SDS gel electrophoresis, were dissolved in 0.1 M NaCl, 0.1 M NaH $CO_3$ and coupled to Sepharose CL-4B which had been activated with 2 g CNBr/100 ml packed Sepharose. Before use, monoclonal antibody Sepharose CL-4B was packed in columns made from 1 ml tuberculin syringes.

Immunoadsorbance Using MAb

The lectin-purified antigen mixture described above was passed through a column, prepared as described above, containing 0.4 ml of Sepharose CL-4B having 0.9 mg M1/69.16 antibody/ml Sepharose coupled to it, and then washed with 1 ml of 0.1% NaDC, 0.01 M tris HCl at pH 8.2. This resulted in the complete removal from the antigen mixture of M1/69.16 antigen, but had no effect on M1/9.3 or M1/70 antigen.

To remove M1/9.3 antigen, an M1/89.18 column was used. The M1/69.16-free antigen mixture was passed through a column, prepared as described above, containing 0.5 ml of Sepharose CL-4B having 0.9 mg M1/89.18 antibody/ml Sepharose coupled to it, and then through 0.8 ml of Sepharose CL-4B having 0.9 mg of fresh M1/89.18 antibody/ml Separose coupled to it. The resulting antigen mixture was found to be completely free of M1/9.3 antigenic material, while only slightly depleted in M1/70 antigen.

Immunization

The purified antigen mixture from the last step described above was dialyzed for 7 days against 2 daily changes of 0.01 M tris HCl, pH 8.2, to remove NaDC. Two (Lewis×BN) $F_1$ rats were primed by being inoculated with 40 μg of the antigen mixture emulsified in complete Freund's adjuvant on days 0 and 18, and bleeds were taken on day 35. Four months later one of the rats was inoculated, i.v., with 100 μg of the antigen mixture in saline and splenectomized for cell fusion 3 days later.

Monoclonal Antibodies to Purified Antigen

Fusion of spleen cells to NSI myeloma cells was carried out as described in Springer et al. (1978) *Eur. J. Immunol.* 8, 539. NSI cells have been deposited with the Cell Line Distribution Center, Salk Institute. The hybrid cells, designated the M3 hybridoma cultures, were aliquoted into 5×96 well microculture plates, and the 86 cultures exhibiting the highest binding, in the indirect binding assay described in Springer et al. (1978) *Eur. J. Immunol.* 8, 539, were saved. Culture medium supernatants were next screened for immunoprecipitation of $^{125}I$ (lactoperoxidase)labelled PEC surface antigens, and those cultures corresponding to supernatants failing to precipitate those antigens discarded.

Of the remaining M3 cultures, media supernatants from five precipitated a complex of 190,000 and 105,000 MW polypeptides from the antigen mixture used to inoculate the mice, thus demonstrating the same specificity as M1/70; the antibodies from these cultures were designated anti-Mac-1.

The medium supernatants from eleven additional M3 cultures all precipitated a 32,000 MW polypeptide from the inoculating antigen mixture. Two of these hybrids, M3/31 and M3/38, were successfully cloned and stabilized. The antibodies from these cultures were designated anti-Mac-2.

One culture, M3/37, precipitated a 180,000 MW polypeptide, but was unstable. An additional culture, M3/84, precipitated a 110,000 MW polypeptide, Mac-3, and was successfully cloned; the antibody from this culture was designated anti-Mac-3.

Further Cascade Purification

Monoclonal antibody purified from the media supernatant of any of the new stable hybrids, for example, anti-Mac-3, could then be coupled to a CNBr-treated Sepharose column as previously described, and a sample of the purified antigen mixture previously used to immunize animals, as described above, could then be passed through the monoclonal antibody column, removing antigens specific to the immobilized antibody. The further purified antigen mixture could then be used to immunize additional animals to produce still more desired monoclonal antibodies. The process could be repeated indefinitely, until all of the desired monoclonal antibodies specific to the antigen mixture had been isolated.

What is claimed is:

1. A method of preparing one or more monoclonal antibodies, said method comprising the steps of
   (a) providing a cell-free liquid containing a plurality of different antigens,
   (b) contacting a sample of said liquid with one or more monoclonal antibodies each specific to a said antigen to form complexes between said monoclonal antibodies and antigens present in said liquid and then removing said complexes from said liquid to yield a partially purified liquid substantially free of antigens specific to said one or more monoclonal antibodies, (c) immunizing an animal with said partially purified liquid, (d) fusing spleen cells from said immunized animal to myeloma cells to form hybridomas capable of producing monoclonal antibodies, (e) culturing said hybridomas to produce said monoclonal antibodies, (f) isolating one or more of said monoclonal antibodies, (g) repeating steps (b) through (f) in sequence, at least once, using in step (b) at least one monoclonal antibody of step (f) in the previous sequence, and (h) terminating said method when, or before, said liquid contains one antigen.

* * * * *